US009805462B2

(12) United States Patent
Sezginer et al.

(10) Patent No.: US 9,805,462 B2
(45) Date of Patent: Oct. 31, 2017

(54) MACHINE LEARNING METHOD AND APPARATUS FOR INSPECTING RETICLES

(71) Applicant: KLA-Tencor Corporation, Milpitas, CA (US)

(72) Inventors: Abdurrahman Sezginer, Monte Sereno, CA (US); Gang Pan, Santa Clara, CA (US); Bing Li, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/484,017

(22) Filed: Apr. 10, 2017

(65) Prior Publication Data

US 2017/0221190 A1    Aug. 3, 2017

Related U.S. Application Data

(63) Continuation of application No. 15/221,304, filed on Jul. 27, 2016, which is a continuation of application
(Continued)

(51) Int. Cl.
*G06T 7/00* (2017.01)
*G06K 9/62* (2006.01)
(Continued)

(52) U.S. Cl.
CPC ......... *G06T 7/001* (2013.01); *G01N 21/9501* (2013.01); *G01N 21/95607* (2013.01);
(Continued)

(58) Field of Classification Search
None
See application file for complete search history.

(56) References Cited

U.S. PATENT DOCUMENTS 5,563,702 A    10/1996    Emery et al.
5,737,072 A    4/1998    Emery et al.
(Continued)

FOREIGN PATENT DOCUMENTS

| JP | 2000-346627 A | 12/2000 |
| JP | 2007-212201 A | 8/2007 |
| WO | 2013142079 A1 | 9/2013 |

OTHER PUBLICATIONS

Sen, Suman K. Classification on manifolds. Diss. University of North Carolina at Chapel Hill, 2008.*
(Continued)

*Primary Examiner* — Kim Vu
*Assistant Examiner* — Nathan Bloom
(74) *Attorney, Agent, or Firm* — Kwan & Olynick LLP

(57) ABSTRACT

Apparatus and methods for inspecting a specimen are disclosed. An inspection tool is used at one or more operating modes to obtain images of a plurality of training regions of a specimen, and the training regions are identified as defect-free. Three or more basis training images are derived from the images of the training regions. A classifier is formed based on the three or more basis training images. The inspection system is used at the one or more operating modes to obtain images of a plurality of test regions of a specimen. Three or more basis test images are derived from to the test regions. The classifier is applied to the three or more basis test images to find defects in the test regions.

26 Claims, 8 Drawing Sheets

Related U.S. Application Data

No. 14/274,972, filed on May 12, 2014, now Pat. No. 9,430,824.

(60) Provisional application No. 61/823,156, filed on May 14, 2013.

(51) Int. Cl.
| | | |
|---|---|---|
| *G03F 1/84* | (2012.01) | |
| *G03F 7/20* | (2006.01) | |
| *G01N 21/956* | (2006.01) | |
| *G01N 21/95* | (2006.01) | |
| *G06N 99/00* | (2010.01) | |

(52) U.S. Cl.
CPC ............. *G03F 1/84* (2013.01); *G03F 7/7065* (2013.01); *G06K 9/6232* (2013.01); *G06N 99/005* (2013.01); *G01N 2021/95676* (2013.01); *G01N 2201/12* (2013.01); *G06T 7/0008* (2013.01); *G06T 2207/20081* (2013.01); *G06T 2207/30148* (2013.01)

(56) References Cited

U.S. PATENT DOCUMENTS

| | | | |
|---|---|---|---|
| 6,349,265 B1 | 2/2002 | Pitman et al. | |
| 9,430,824 B2 | 8/2016 | Sezginer et al. | |
| 2003/0086081 A1 | 5/2003 | Lehman | |
| 2003/0185432 A1 | 10/2003 | Hong et al. | |
| 2004/0156540 A1* | 8/2004 | Gao | G06T 7/0004 382/145 |
| 2005/0134840 A1* | 6/2005 | Yu | G03F 1/84 356/237.2 |
| 2006/0067570 A1* | 3/2006 | Onishi | G06T 7/001 382/147 |
| 2006/0203233 A1 | 9/2006 | Yu | |
| 2006/0287751 A1 | 12/2006 | Dishner et al. | |
| 2007/0133860 A1 | 6/2007 | Lin et al. | |
| 2007/0288219 A1* | 12/2007 | Zafar | G03F 1/84 703/14 |
| 2008/0250384 A1 | 10/2008 | Duffy et al. | |
| 2009/0290784 A1* | 11/2009 | Lin | G06T 7/001 382/149 |
| 2010/0119144 A1* | 5/2010 | Kulkarni | H01L 21/67005 382/149 |
| 2010/0226562 A1* | 9/2010 | Wu | G01N 21/95607 382/149 |
| 2011/0224932 A1 | 9/2011 | Huet et al. | |
| 2011/0299758 A1* | 12/2011 | Shi | G03F 1/84 382/144 |
| 2012/0002860 A1 | 1/2012 | Sakai et al. | |
| 2012/0057773 A1* | 3/2012 | Langmatz | G06T 7/001 382/141 |
| 2013/0035876 A1 | 2/2013 | Huang et al. | |
| 2013/0082174 A1* | 4/2013 | Chen | H01L 22/12 250/307 |
| 2013/0236083 A1 | 9/2013 | Wang et al. | |
| 2013/0322728 A1* | 12/2013 | Jacobs | A61B 5/055 382/132 |
| 2014/0301630 A1* | 10/2014 | Kulkarni | G06T 7/0004 382/149 |
| 2014/0341462 A1 | 11/2014 | Sezginer et al. | |
| 2016/0335753 A1 | 11/2016 | Sezginer et al. | |

OTHER PUBLICATIONS

Vemulapalli, Raviteja, Jaishanker K. Pillai, and Rama Chellappa. "Kernel learning for extrinsic classification of manifold features." Proceedings of the IEEE Conference on Computer Vision and Pattern Recognition. 2013.*

"U.S. Appl. No. 14/274,972, Non Final Office Action dated Dec. 4, 2015", 15 pages.

"U.S. Appl. No. 14/274,972, Notice of Allowance dated Apr. 29, 2016", 7 pages.

"U.S. Appl. No. 15/221,304, Notice of Allowance dated Jan. 13, 2011", 11 pages.

"Int'l Application Serial No. PCT/US2014/037915, Search Report & Written Opinion dated Jan. 28, 2015", 9 pages.

* cited by examiner

MACHINE LEARNING METHOD AND APPARATUS FOR INSPECTING RETICLES

CROSS-REFERENCE TO RELATED APPLICATIONS

This application is a continuation of and claims the benefit under 35 U.S.C. §120 of U.S. application Ser. No. 15/221,304, filed 27 Jul. 2016, entitled "Machine Learning Method and Apparatus for Inspecting Reticles" by Abdurrahman (Apo) Sezginer et al., which is a continuation of and claims the benefit under 35 U.S.C. §120 of U.S. application Ser. No. 14/274,972, filed 12 May 2014, entitled "Machine Learning Method and Apparatus for Inspecting Reticles" by Abdurrahman (Apo) Sezginer et al., which claims priority under 35 U.S.C. §119 of prior U.S. Provisional Application No. 61/823,156, filed 14 May 2013, entitled "Machine Learning Method and Apparatus for Inspecting Reticles" by Abdurrahman (Apo) Sezginer et al. These applications are herein incorporated by reference in their entireties for all purposes.

TECHNICAL FIELD OF THE INVENTION

The invention generally relates to the field of semiconductor reticle inspection. More particularly the present invention relates to techniques for inspecting reticles, including non-repeating patterns, when a design database is not present.

BACKGROUND

Fabricating integrating circuits involves depositing and patterning layers of metal, dielectric, and semiconductor materials onto a substrate or wafer, such as silicon. The layers are patterned using optical lithography, which projects the image of a reticle onto the wafer to be patterned. Due to the decreasing size of semiconductor devices, defects which cause faults in the device are becoming progressively smaller.

An integrated circuit is typically fabricated from a plurality of reticles. On the order of 50 lithography steps are used in the fabrication of an advanced CMOS logic chip. Each reticle encodes the pattern of one physical layer of an integrated circuit. In the case of multi-patterning, more than one lithography step, hence more than one reticle, are used to pattern one physical layer. Generation of reticles and subsequent optical inspection of such reticles are standard steps in the production of semiconductors. A reticle itself is patterned by e-beam lithography using a vector-shaped beam tool, or in the case of less critical layers, by optical lithography using a laser scanner. Designers aided by electronic design automation (EDA) software start with the functional description of the IC, and after many steps produce a physical layout of each layer of the IC. The physical layout is represented by a database containing layers, and each layer containing a set of polygons. Further EDA processes such as optical proximity correction, mask proximity correction or biasing, and fracturing, convert the physical layout to data that controls the reticle writer. The reticle writer data is also contained in a polygon database. A reticle inspection system inspects the finished reticle for defects that may have occurred during its production.

A reticle needs to be fabricated free of defects in order to be used to fabricate defect-free wafer devices. Additionally, a reticle may become defective after use. Thus, there is a continuing need for improved reticle inspection techniques. A reticle is exposed to intense deep-ultraviolet radiation in the lithography projector. Photo-chemical reactions can deposit residues on the reticle. Such residues are called haze. Electrostatic discharge can damage a reticle if it is improperly handled. Therefore, a reticle is typically inspected at the wafer fab upon receipt, and periodically thereafter. A reticle under inspection in the wafer fab has already passed multiple inspections at the time of its fabrication. The objective of the inspection at the wafer fab is to detect defects that may have developed during the shipment or use of the reticle that was once known to be defect-free.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting a specimen is disclosed. An inspection tool is used at one or more operating modes to obtain images of a plurality of training regions of a specimen, and the training regions are identified as defect-free. Three or more basis training images are derived from the images of the training regions. A classifier is formed based on the three or more basis training images. The inspection system is used at the one or more operating modes to obtain images of a plurality of test regions of a specimen. Three or more basis test images are derived from the test regions. The classifier is applied to the three or more basis test images to find defects in the test regions.

In a specific implementation, the classifier includes mapping the three or more basis training images to a plurality of voxels of a three or more dimensional space and assigning an observation indicator to each voxel so as to specify whether such voxel is defined as a non-defective voxel that is observed in the training set. In a further aspect, forming the classifier further includes healing a plurality of holes in the non-defective voxels by changing an indicator of each voxel of each hole from specifying such voxel is not observed in the training set to specifying that such voxel is a non-defective voxel. In a further aspect, forming the classifier further includes performing a distance transformation to assign a distance value to each voxel based on such voxel's distance to a non-defective voxel. In yet a further aspect, a defect is found when a particular voxel has a distance value that is above a predefined threshold. In another example, forming the classifier comprises approximating a set of feature vectors that correspond to the non-defective voxels with a collection of subsets of affine-linear spaces.

In another embodiment, the method includes (i) forming each of a plurality of classifiers based on a plurality of different sets of the three or more basis training images and (ii) applying the plurality of classifiers to the three or more basis test images to find defects in the test regions. In another example, a space-partitioning data structure is formed from the classifier.

In another implementation, forming the classifier comprises (i) clustering a set of feature vectors that are based on the basis training images into a plurality of clusters, (ii) determining a cluster center of each cluster's feature vectors, (iii) for each cluster, determining a plurality of cluster vectors from each cluster center to the cluster's feature vectors, and (iv) for each cluster, determining an affine-linear space that includes the cluster's cluster center and that is spanned by a plurality of principal components of the cluster's cluster vectors. Applying the classifier to the three or more basis test images is based on a distance between each test vector of the three or more basis test images and a nearest affine-linear space.

In another example, forming the classifier comprises (i) minimizing a norm of distances from a affine linear space to a plurality of feature vectors from the three or more basis training images, (ii) discarding a set of the feature vectors for which a distance is highest, and (iii) repeating the step for minimizing the norm of distance to refine a plurality of affine-linear spaces to better fit remaining ones of the feature vectors until the feature vectors are fitted to a final set of the affine-linear spaces within a predefined tolerance level.

In another embodiment, the classifier includes three or more dimensions of feature vectors that each has a transmitting image value, a reflecting image value, and a transformed image value based on transformation of a transmitting or reflecting image value. In a further aspect, each transformed image value is determined by one of the following: $\|\nabla T\|$, $\|\nabla R\|$, $\nabla^2 T$, $\nabla^2 R$, wherein T is a transmitting image value and R is a reflecting image value. In another embodiment, the one or more operating modes are selectable to differ in one or more of the following qualities or quantities: a reflecting mode, a transmitting mode, a brightfield mode, a darkfield mode, an illumination numerical aperture, an illumination pupil pattern, an illumination polarization, a collection numerical aperture, a collection pupil filter amplitude and phase, a collection analyzer, and a focus.

In certain embodiments, the invention pertains to a system for inspecting a photolithographic specimen. The system includes at least one memory and at least one processor that are configured to perform at least some of the above described operations. In other embodiments, the invention pertains to computer readable media having instructions stored thereon for performing at least some of the above described operations.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Certain embodiments of the present invention include inspection techniques and apparatus for finding defects in non-repeating patterns without use of a design database. One inspection technique includes machine learning using classifiers that are formed from three or more dimensional feature vectors based on reflected (R) and transmitted (T) images or signals from one or more inspection modes and/or signals that are derived from such R or T images. One or more multidimensional classifiers can then be used to locate defects in a corresponding multidimensional space of features vectors obtained from a reticle inspection of unknown test regions.

Figure 1:
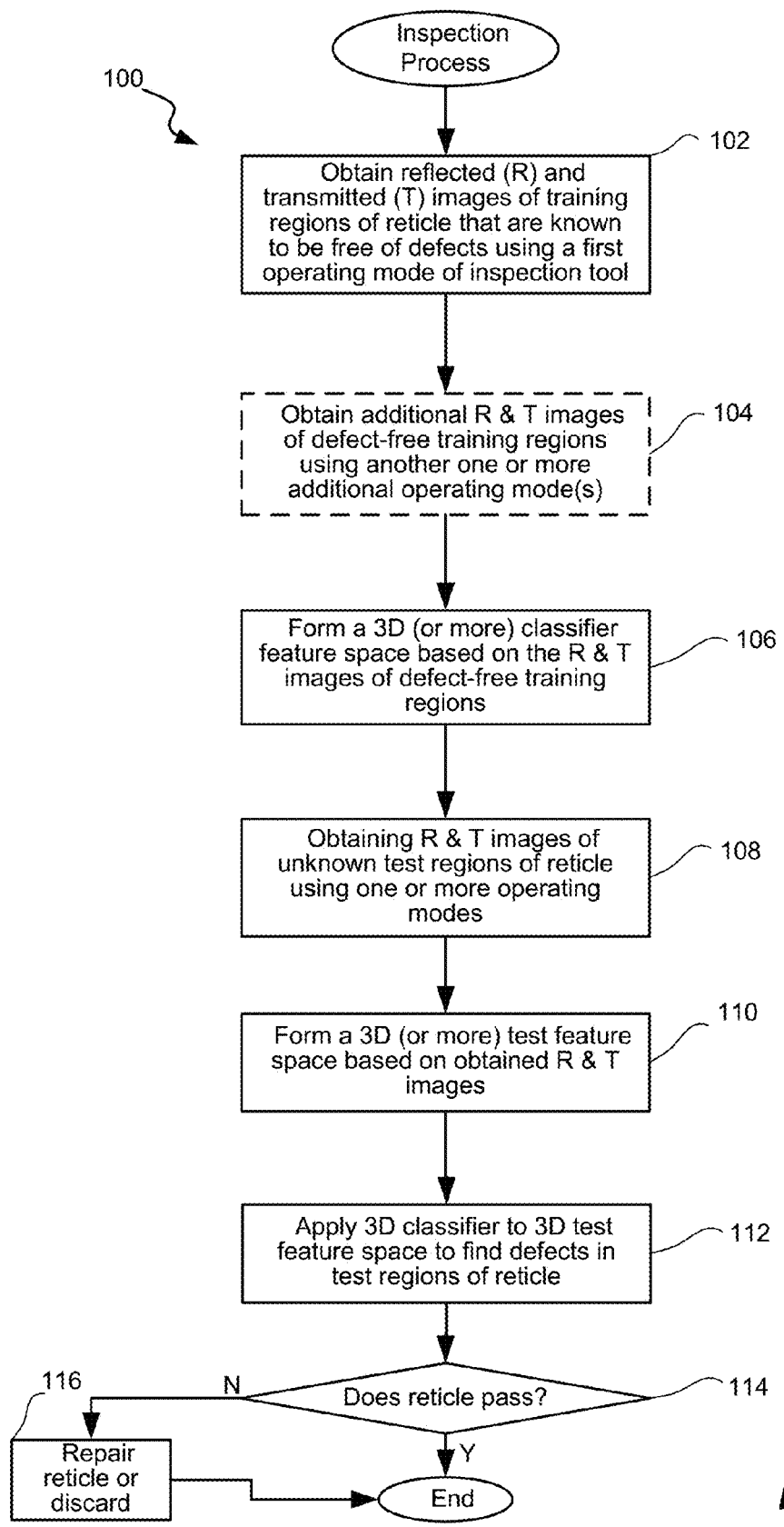
FIG. 1 is a flow chart illustrating an inspection process in accordance with one embodiment of the present invention.

FIG. 1 is a flow chart illustrating an inspection process 100 in accordance with one embodiment of the present invention. Initially, R and T images of training regions of a reticle are obtained in operation 102. The training regions are known to be free of defects. For instance, an operator may select one or more regions of the reticle that are known to be defect-free as a training set of defect-free regions.

Generally, the training regions include a representative sampling of defect-free areas of a selected number of substrates of the same type to account for production tolerances. The training regions may originate from a single sample substrate. However, the use of several sample substrates may provide a better statistical average and the possibility of overcoming the inclusion of a defect on one of the sample substrates.

For instance, specific reticle regions may have been previously inspected using any suitable inspection technique and deemed to not contain any defects that would affect yield or cause a printable error on the wafer. A reticle may be verified or defined as having substantially no degradation or defects by any suitable manner. For example, a reticle is rigorously inspected when it is manufactured at a mask shop. Mask shop inspection may use the die-to-die mode, wherein images of two dies on the reticle that are expected to be identical are compared. Alternatively, mask shop inspection may use die-to-database inspection, where the image of the reticle is compared to the mask database. The training regions can be selected as part of the mask-shop inspection or immediately after passing the mask shop inspection, when the reticle is known to be defect-free. The training regions can then be used for subsequent wafer fab inspections. Alternatively, a training region of a previously inspected reticle may be assumed to be defect-free with no verification since the probability of encountering a defect in a small portion of the reticle is small. For example, the image of a reticle may contain $10^{12}$ pixels and the training region may contain $10^7$ pixels, and there may be 10 defects on the reticle. The probability of one of the defects being in the training region is $10^{-4}$.

An optical inspection tool may be used to obtain R and T images or signals from reticle regions in any suitable manner. For instance, illumination light may be directed towards particular reticle regions and light reflected from the reticle may then be detected by one or more detector systems. Opaque and semi-transparent structures or defects on the reticle may reflect light back to one or more detector systems. Certain illumination light portions may also be transmitted through portions of the reticle, such as transparent or semi-transparent pattern or defect portions. Such transmitted light portions may be detected by one or more detector systems. The transmitted and reflected light may be detected simultaneously or separately.

Additional R and/or T images of the defect-free regions may optionally be obtained under one or more other operating modes in operation 104. For example, different operating configurations, such as focus, illumination wavelength, illumination pupil shape, collection pupil shape, illumination polarization, analyzer setting, numerical aperture of illumination or collection pupil, imaging pupil filter setting, etc. may be used to obtain different sets of R and/or T images or signals. A low numerical aperture (NA) inspection (e.g., that is similar to a lithography tool's NA) may also be used to collect T and/or R images or signals. For instance, a reticle plane inspection at an NA of 0.85 may be used to collect R and T images, and a low NA inspection at an NA of 0.3375 may be used to collect T images.

A 3D (or higher dimensional) classifier may then be formed based on the R and T images of the defect-free training regions in operation 106. The dimensions of a 3D classifier, for example, may be formed from the R and T image values and either another set of R and T images that were obtained in a different inspection mode and/or from other dimension values that are derived from the R or T images.

Figure 2:
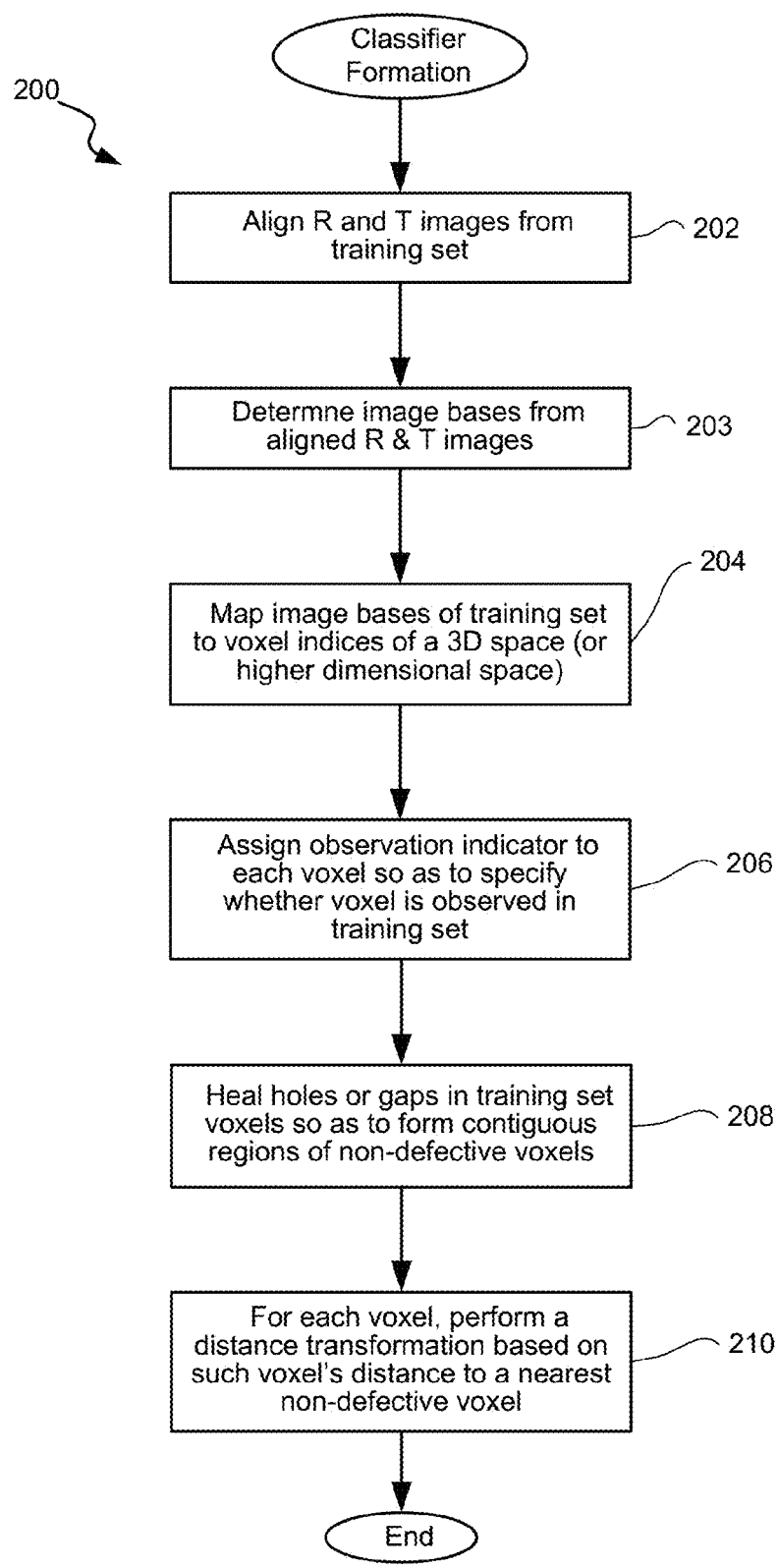
FIG. 2 is a flow chart illustrating a procedure for forming a classifier in accordance with one embodiment of the present invention.

FIG. 2 is a flow chart illustrating a procedure for forming a classifier in accordance with one embodiment of the present invention. Initially, the obtained R and T images from the training set may be aligned in operation 202. The R & T images are generally aligned with respect to each other so that R and T values for a same reticle position are aligned to each other. Any suitable approach may be used to align the images to a same coordinate system or origin across inspections. For example, each inspection can align the reticle so that images are obtained relative to a same origin on the reticle. The reticle origin may take the form of one or more reference marks for aligning the reticle. Alignment is preferably performed with sub pixel resolution by an image computer. Images may be continuously shifted, e.g., using either a sync filter or a Fourier transform, so as to maximize their correlation.

The coordinates (x,y) of each aligned image indicate the position of a feature on the reticle and on the detector. A convenient unit for (x,y) is pixels. Usually (x,y) have integer values, but the image can be interpolated to fractional-pixel coordinates. R(x,y) denotes the reflected light intensity image. Intensity R(x,y) may be measured in gray scales or ADC (analog to digital conversion) counts. Similarly, T(x,y) denotes the transmitted light intensity at pixel (x,y) and can be measured in gray scales or ADC counts.

Image bases may then be determined from the aligned R and T images in operation 203. The image bases may be formed from any suitable R and/or T-based images, such as one or more R and/or T images obtained from one or more inspection modes and/or various transformations of R and/or T images. Said in another way, each image pixel (x,y) may be assigned a feature vector after alignment. This vector may be a three-tuple in one embodiment. Two of the numbers in the three-tuple may be R and T light intensity, R(x,y) and T(x,y). In specific embodiments, the third number may be defined as one of $\|\nabla T\|$, $\|\nabla R\|$, $\nabla^2 T$, $\nabla^2 R$ defined as:

$$\|\nabla T\|(x, y) = \sqrt{[T(x+1, y) - T(x-1, y)]^2 + [T(x, y+1) - T(x+1, y-1)]^2}$$

$$\|\nabla R\|(x, y) = \sqrt{[R(x+1, y) - R(x-1, y)]^2 + [R(x, y+1) - R(x+1, y-1)]^2}$$

$$\nabla^2 T(x, y) = T(x+1, y) + T(x-1, y) + T(x, y+1) + T(x+1, y-1) - 4T(x, y)$$

$$\nabla^2 R(x, y) = R(x+1, y) + R(x-1, y) + R(x, y+1) + R(x+1, y-1) - 4R(x, y)$$

Another base image can be formed by a linear or non-linear image transformation applied to R(x,y) and T(x,y). The general form of a linear transformation is:

$$u(x,y) = (g_R \otimes R)(x,y) + (g_T \otimes T)(x,y)$$

where $g_R$ and $g_T$ are 2-dimensional filters and the operator $\otimes$ indicates 2-dimensional convolution.

In other embodiments, the third number may be R or T light intensity, or any one of $\|\nabla T\|$, $\|\nabla R\|$, $\nabla^2 T$, $\nabla^2 R$, collected under a different inspection mode (such as low NA or other operating modes). Of course, each feature vector may have more than three dimensions based on any of the above described feature values. Each of these quantities can correspond to an image collected from the reticle or a transformed image. The collection of these images can be referred to as the "image basis" or one of them as a base image or image base. The list above is not an exhaustive list of image bases.

Figure 3:
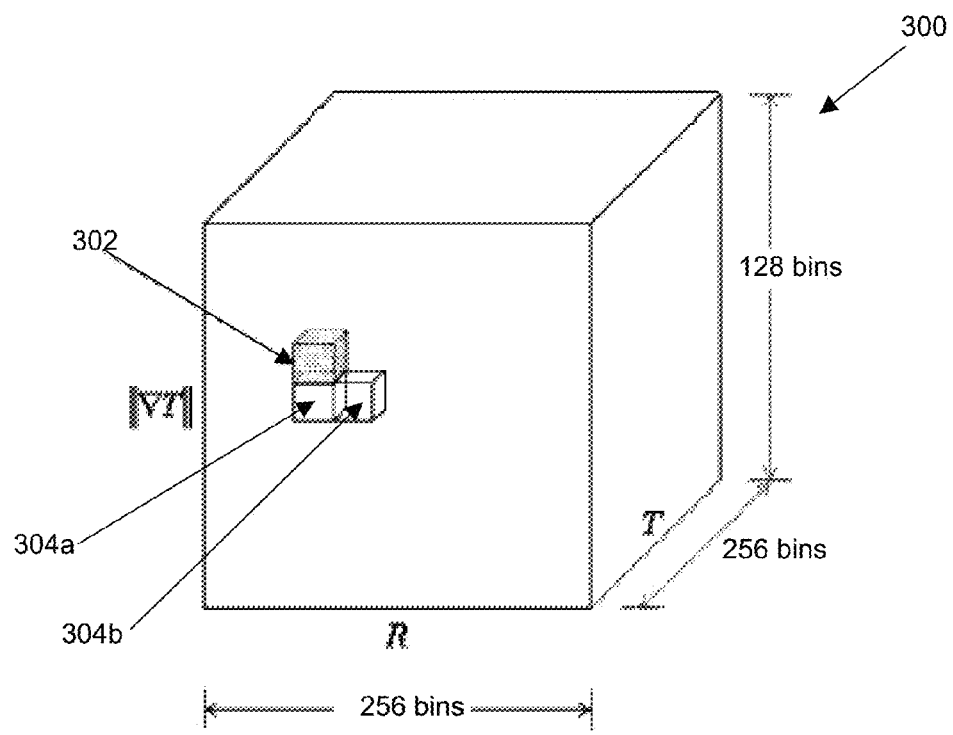
FIG. 3 shows an example of a 3D feature space into which the training set's feature vectors are mapped in accordance with a specific embodiment.

The image bases of the training set may then be mapped to voxel indices of a 3D space (or higher dimensional space) in operation 204. A voxel is a set of feature vectors. FIG. 3 shows an example of a 3D feature space 300 into which the training set's feature vectors are mapped in accordance with a specific embodiment. Each array element is generally associated with a set of (a voxel of) feature vectors. In this example, the set of feature vectors correspond to the image parameters (T,R,$\|\nabla T\|$), and the center of each voxel has a distinct value of (T,R,$\|\nabla T\|$). Each voxel may typically include other values, in addition to the center voxel value, which may be selected based on the desired array size.

The array may have any number of voxels. The illustrated array 300 has 256×256×128 voxels. Other voxel dimensions may be used. Given images R(x,y), T(x,y), the values (T,R,$\|\nabla T\|$) may be scaled to convert image values to voxel indices. The scaling can be static during the inspection of a reticle. The scaling may be selected such that three-tuples for the training feature vectors either never or rarely fall outside the selected three-dimensional array.

An observation indicator may be assigned to each voxel of the 3D feature space so as to specify whether the voxel is observed in the training set in operation 206. That is, each voxel can be associated with an indicator specifying whether such voxel corresponds to a defect-free feature vector from the training set or not. For instance, each voxel may also be configured to hold (or be associated with) a Boolean value of 0 or 1 that indicates whether such voxel has been observed or not observed, respectively, in the training set. As shown, voxel 302 corresponds to a non-defective voxel from a training reticle region that is defect-free and may be given a value of 0. In contrast, voxels 304a and 304b do not correspond to non-defective voxels and may be given values of 1.

In an embodiment, each voxel may also be assigned the number of times it is observed in the training data. Voxels that are rarely observed in the training data may be due to defects that have not been removed from the training data. In a specific implementation, voxels that are observed fewer than m times, and that are more distant than d voxels to the nearest voxel that has been observed in the training data, may be treated as never observed in the training data. For instance, voxels that infrequently occur in the training set and are a significant distance from a nearest training set voxel may be assigned a 1 Boolean value. The parameters n and d may be pre-determined values, such as 1 and 3, respectively, that are based on past verified results.

Referring back to FIG. 2, holes or gaps in the training set voxels may be healed so as to form simple contiguous regions of non-defective voxels in operation 208. Non-defective voxels are expected to form one or a few simple connected regions. Insufficient sampling during training may leave holes in the set of non-detective voxels. Any suitable healing process may be used to fill these holes.

A healing process may include using twice up-sampled images for training. For a particular band limited signal that is sampled at a particular spatial frequency, additional points can be interpolated between each pair of sample points in a twice up-sampling of the signal based on Nyquist's theorem. Different levels of up-sampling may be used. Up-sampling images would more completely fill in the point cloud and cover the set of non-defective voxels. In an alternative approach, the images R(x,y) and T(x,y) may be shifted by the same vector of a fractional pixel size to achieve more interpolated sampling points. The shifted images are then appended to the training data.

Figure 4:
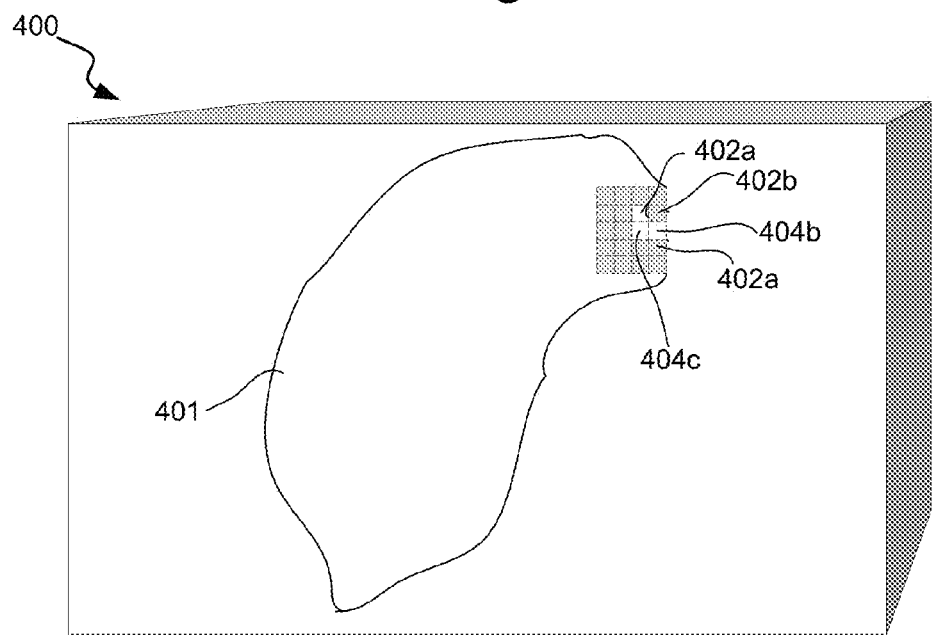
FIG. 4 illustrates an array of voxels having voxels that were observed in the training set.

In another healing example, an array of voxels is scanned one dimension at a time along a line. Gaps between non-defective voxels are set to "non-defective" if the gap is narrower than a pre-determined value, e.g., 8 voxels. Other values may be used. FIG. 4 illustrates an array of voxels 400 having non-defective voxels 401 that were observed in the training set. Although the non-defective voxel set 401 would typically be three-dimensional, only a 2D surface of the voxels 401 is shown. These voxels 401 that were designated as being present in the non-defective training set have single voxel-wide gaps 404a, 404b, and 404c. For instance, voxel gap 404b is positioned between non-defective voxels 402b and 402a. Since these gaps are each the same size as a single voxel, these gap voxels may be also be designated as being observed in the training set if the gap is threshold is 2 or more voxels.

In another example, a region of non-defective voxels may be dilated by k voxels, such as 8 voxels, and then eroded by k-voxels. Dilation followed by erosion fills the gaps.

A distance transformation may be performed on each voxel based on such voxel's distance to a nearest non-defective voxel in operation 210. In one implementation, the voxels that have been observed during training or healed to be designated as non-defective are assigned the value 0. The voxels that are adjacent to the voxels that have been assigned zero are assigned the value 1. The voxels that are adjacent to the ones that are assigned 1 and that have not been assigned any value so far are assigned the value 2, and so on. In this manner, each voxel is encoded by its distance to the nearest non-defective voxel. The higher the distance, the more likely that the voxel indicates a defect. Other types of distance values are contemplated. For example, the shortest Euclidian distance between the test voxel and the non-defective voxels may be used.

In another embodiment, voxels have only a Boolean value of 1 or 0, but the region of "non-defective" voxels is dilated to avoid false-positive defect detection. Dilation means voxels that are adjacent to "non-defective" voxels are set to a "non-defective" value (0), while the remaining voxels are set to a defective value (1). In an embodiment, two voxels are considered adjacent if they have a common vertex. In three-dimensions, each voxel has 33−1=26 adjacent voxels. Dilation can be formed recursively.

Figure 5:
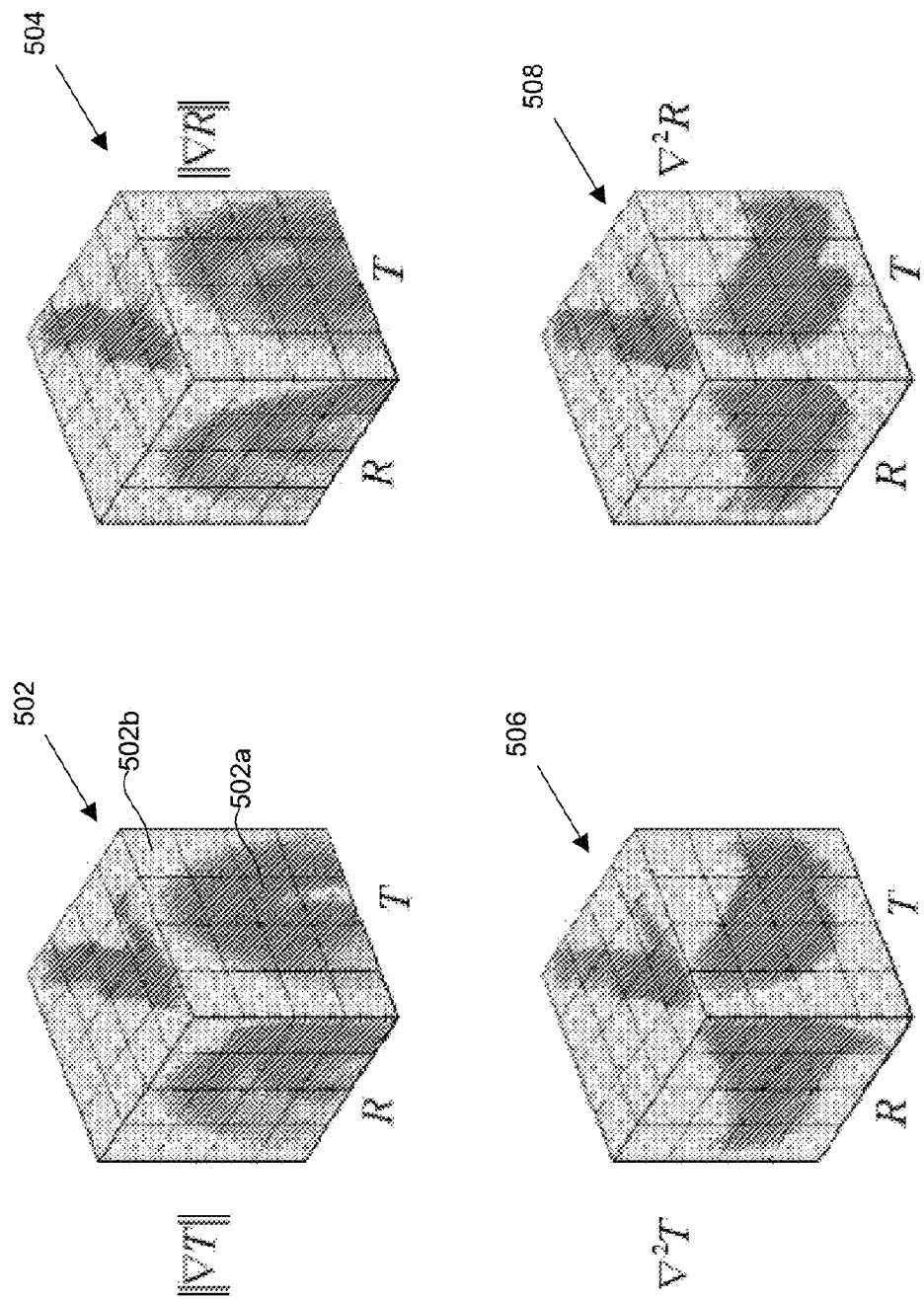
FIG. 5 shows four possible 3D classifiers in accordance with certain embodiments of the present invention.

Processing the voxels in the 3D (or more) feature space with respect to the training set will result in a classifier that can be used to detect defects in unknown regions of a reticle. FIG. 5 shows four possible three-dimensional classifiers 502, 504, 506, and 508 in accordance with certain embodiments of the present invention. The different classifiers have different feature vectors. Any three or more image bases can be used to form a 3D (or more) classifier. For instance, classifier 502 has feature vectors that correspond to values $(T,R,\|\nabla T\|)$. Classifier 504 has feature vectors corresponding to values $(T,R,\|\nabla R\|)$. Likewise, classifier 506 corresponds to values $(T,R,\|\nabla^2 T\|)$, and classifier 308 corresponds to $(T,R,\|\nabla^2 R\|)$.

Although only three dimensions are shown for the illustrated classifiers, other dimensions may correspond to a plurality of different inspection modes, views, or a transformation of an R- or T-based parameter value. For instance, a fourth dimension can correspond to T at a different inspection mode.

Each classifier includes a set of voxels that have been associated with designations that indicate non-defective regions. In the illustrated classifier examples, the dark regions correspond to non-defective regions. For example, classifier 502 has non-defective voxels in dark region (e.g., 502a). Lighter shaded regions outside of these non-defective regions indicate possible non-defective regions, such as region 502b.

Any of these classifiers can be used to determine whether a test vector corresponds to a defect. Additionally, more than one classifier can be used together. When multiple classifiers are used, their results can be combined with the logical "or" operator or with the logical "and" operator. In the preferred embodiment, a defect can be identified if at least one of the classifiers detects a defect. In another embodiment, a defect can only be identified when all classifiers detect a defect.

Referring back to FIG. 1, R and T images may also be obtained for unknown test regions of a reticle using one or more operating modes in operation 108. For instance, the one or more operating modes that were used for obtaining the training image sets may be used to obtain R and T image sets for the reticle test regions. A 3D test feature space may also be formed based on obtained R and T images in operation 110, and the 3D classifier may be applied to such 3D test feature space to find defects in such test regions of the reticle in operation 112.

During inspection, the R(x,y) and T(x,y) images are aligned. The test image bases are calculated, and the voxel indices are calculated from the test image bases. For each test voxel index, a corresponding classifier distance value may then be retrieved from memory. The retrieved value can be used to determine whether the test image pixel (x,y) corresponds to either a defective or a non-defective portion of the reticle.

In the Boolean classifier example, a 1 or 0 value is retrieved that clearly indicates whether a particular test region voxel is non-defective or defective. In the graded distance approach, a varying integer value that relates to such voxel's distance to a non-defective region voxel is retrieved. A threshold may be applied to the retrieved graded distance value to determine whether the test voxel is a binary "defective" or "non-defective" voxel. For example, a threshold of 1 or 2 may be used. The value of the threshold can be increased to reduce the probability of false-positive defect detection or reduced to reduce the probability of false-negative defect detection. The threshold can be selected by a software slider accessible to an operator and determined based on past results for detecting defects on known samples.

After defects are found, it may then be determined whether the reticle passes inspection in operation 114. For instance, each found defect may be carefully reviewed (e.g., by an operator) to determine whether the reticle is defective and can no longer be used. In a specific implementation, the reticle may be deemed defective when a size or frequency of defective voxels exceeds a particular threshold. If the reticle does not pass, the reticle can either be repaired or discarded in operation 116 and inspection ends. If the reticle passes or after the reticle is repaired/discarded, the inspection process may end. After the reticle (repaired or passing reticle) is again used, the reticle may again be inspected for new defects.

Figure 6:
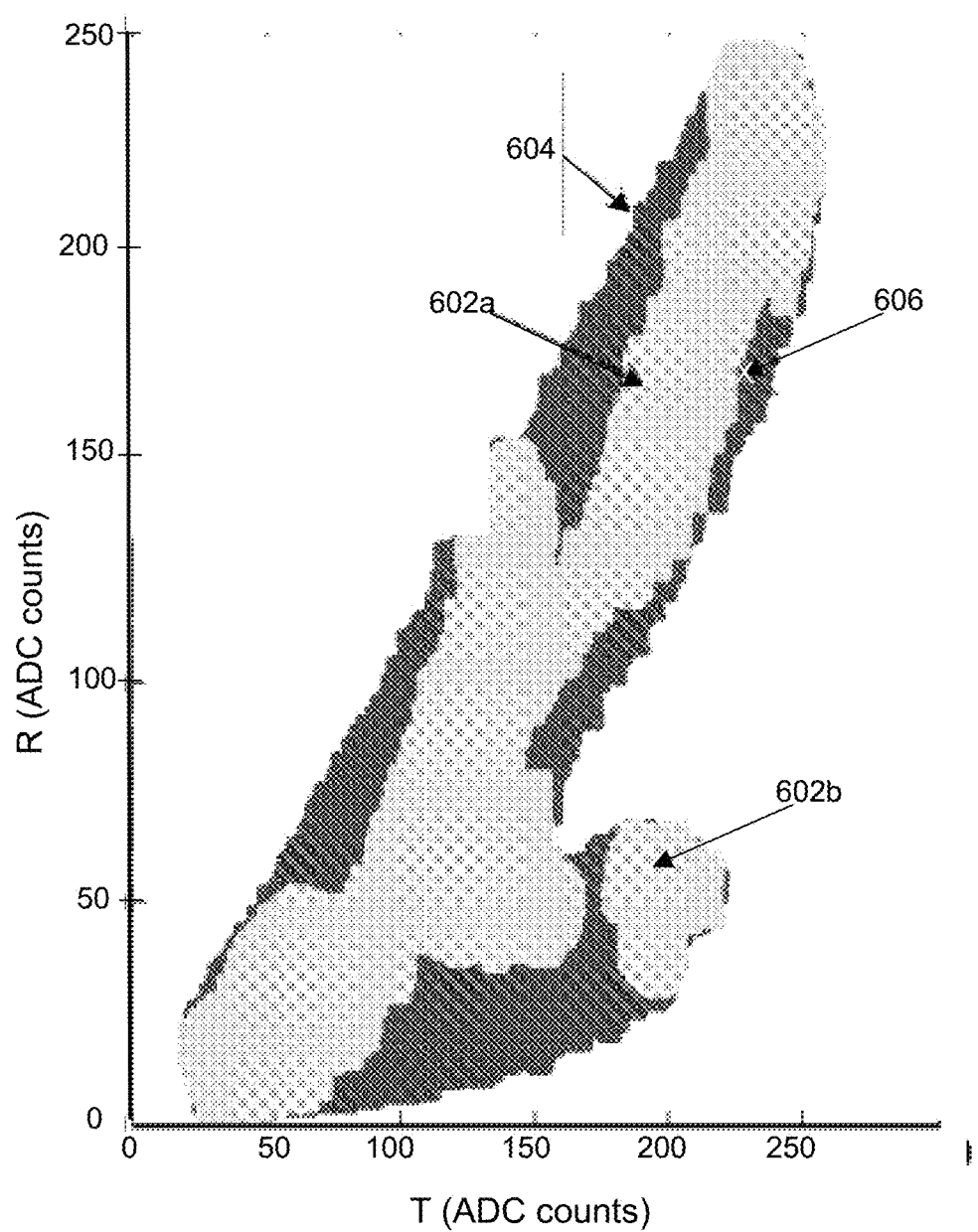
FIG. 6 illustrates a comparison between a 2D and a 3D classifier approach.

Certain embodiments of the present invention provide an improvement over 2D classification using only an (R,T) plane. FIG. 6 illustrates a comparison between a 2D and 3D classifier approach. A 2D (R,T) classifier may include non-defective region 604, which encompasses both the dark colored and gray colored regions. In general, a 2D non-defective region is a projection of the 3D non-defective regions onto a (R,T) plane. As shown, defect 606 appears in this 2D non-defective region 604 and is not detected.

However, when a third dimension is considered without projection, defect detection is determined based on a particular plane of the 3D non-defective classifier that is parallel to the (R,T) plane to which the defect voxel may be compared. As shown, the cut (the intersection) for defect 606 includes only non-defective regions 602*a* and 602*b* (gray color). The cut is a subset of the projection by definition. Since the defect 606 is outside the 3D non-defective region 602*a* and 602*b* for the particular 3D position in the particular plane shown in FIG. 6, the defect is detected. In sum the defect 606 can be detected by the 3D classifier but not by a 2D classifier. Accordingly, the 3D classifier is more sensitive than the 2D classifier.

In an alternative embodiment that uses a high M-dimensional (more than 3) classifier, mechanisms can be used to partition the M-dimensional Euclidean classifier space to minimize the use of computational and storage resources. The classifier point cloud may be represented in any suitable manner. For example, a point cloud (feature vectors) classifier can be organized as a space-partitioning data structure that can be more efficiently searched to determine whether a voxel corresponds to a defect. Partitioned data structures may include, but not be limited to, a k-d tree and its variations, an R-tree and its variations, a VP-tree, etc. During inspection, the distance between a test feature vector and the classifier point cloud can then be calculated efficiently using the organized tree structure.

In a k-d tree partitioning data structure example, every node is a k-dimensional point. At every non-leaf node, a splitting hyperplane divides the feature space into two parts, known as half-spaces. Points to the left of this hyperplane are represented by the left subtree of that node and points right of the hyperplane are represented by the right subtree. The hyperplane direction can be chosen associating every node in the tree with one of the k-dimensions, with the hyperplane perpendicular to that dimension's axis. If an "x" axis split is chosen, all points in the subtree with a smaller "x" value than the node will appear in the left subtree and all points with larger "x" value will be in the right subtree. Same value points can be designated to appear in either the right or left subtree.

A high-dimensional feature space can also be analyzed to construct a manifold from a plurality of approximated small smooth surfaces (or lower dimensional portions) on such high-dimensional feature space. The goal of this embodiment may be to approximate this manifold by a collection of subsets of affine-linear subspaces. For example, the affine-linear subspaces can be tangent subspaces of the manifold at a set of points selected on the manifold. During inspection of a given a test feature vector, a distance from the test point to the nearest affine linear subspace can be computed. If this distance is greater than a threshold, a defect is detected.

Initially, a point cloud of feature vectors can be clustered into points that are close to each other. Any suitable clustering technique may be implemented to cluster the points. Example clustering techniques include k-means, connectivity models, centroid models, distribution models, density models, subspace models, group models graph-based models, etc.

For each cluster, the vectors from the cluster center to the feature vectors in the cluster may be calculated. Principal components of these vectors are approximately tangent to a manifold. The affine-linear space L that includes the cluster center and that is spanned by the principal components is an approximation to the manifold around the cluster center. Alternatively, the vectors that span L may be determined by convex optimization. The cluster center and the vectors that span L are then stored.

Figure 7:
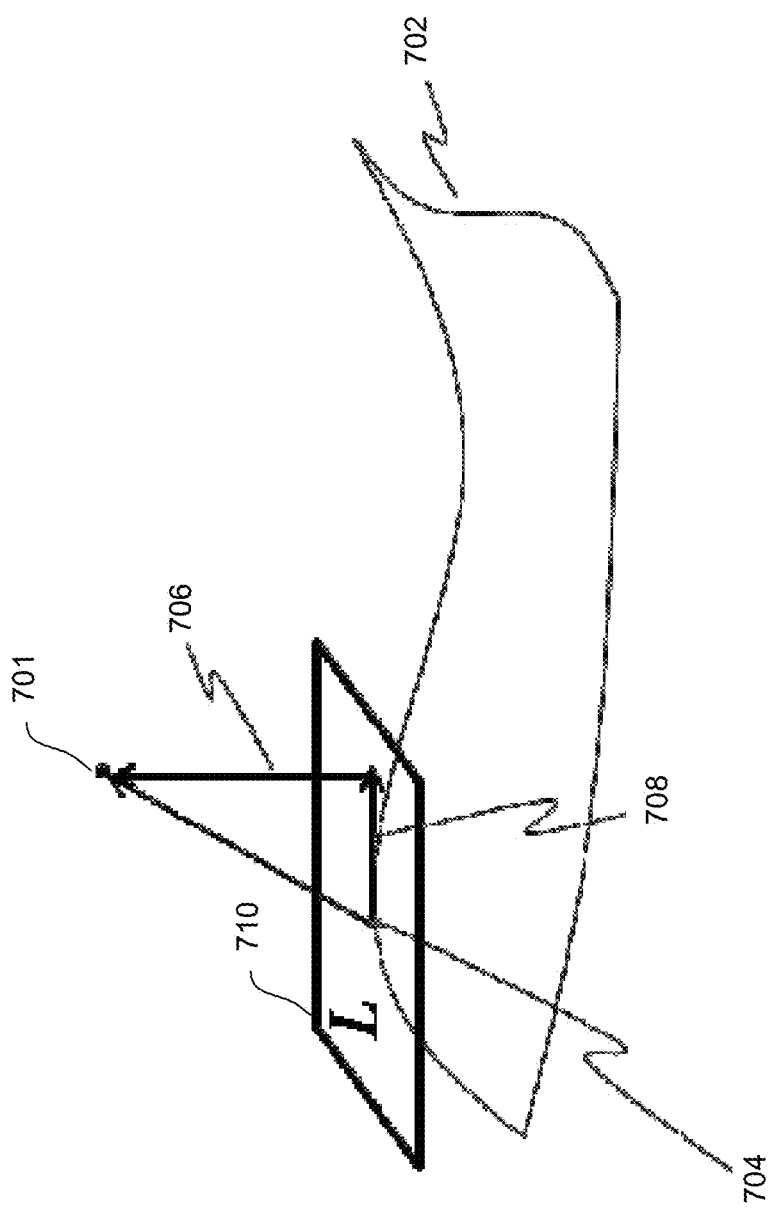
FIG. 7 illustrates a manifold constructed from non-defective feature vectors in accordance with one embodiment.

FIG. 7 illustrates a manifold 702 constructed from non-defective feature vectors in accordance with one embodiment. For example, this manifold 702 includes feature vector 704. During inspection, given a test feature vector 701, the cluster center that is closest to this test feature vector 701 is found. The distance from the feature vector to the affine-linear space L (710) is calculated. This distance is the norm of the residual vector 706. The residual vector 706 is the vector from the test feature vector to its orthogonal projection (708) on L. If the distance exceeds a threshold, a defect is detected.

Any suitable technique may be used to approximate the non-defective feature vectors into a collection of subsets of affine-linear subspaces. For example, the affine-linear subspaces can be tangent subspaces of a manifold at a set of points selected on the manifold. In a second embodiment, the affine linear space that fits as many of the points in the point cloud is determined by solving an optimization problem. Initially, a norm of distances from the affine linear space to the points in the point cloud may be minimized. A fraction of the points in the point cloud for which the distance is largest may then be discarded. Another norm of distances from the affine linear space to the points in the point cloud may be minimized again to refine the affine linear subspaces to better fit the remaining points in the cloud. This process may be repeated iteratively until a new set of affine linear spaces fit the remaining points to a pre-selected tolerance. The points that are fitted well by one affine-linear space form a cluster. Any feature vectors that are not well-fitted with the collection of generated affine-linear spaces may be selected for refitting. A new affine-linear space and the cluster associated with such space may be found for these selected feature vectors. This process may be repeated until all the feature vectors are approximated to a collection of affine-linear subspaces.

Certain embodiments of the present invention provide inspection techniques with improved sensitivity without increasing complexity when inspecting non-repeating patterns without a database.

Images of a reticle may be obtained using any inspection tool, such as an optical inspection system, that is set up in any suitable manner. The inspection system is generally set up with a set of operating parameters or a "recipe." Recipe settings may include one or more of the following settings: a setting for scanning the reticle in a particular pattern, pixel size, a setting for grouping adjacent signals from single signals, a focus setting, an illumination or detection aperture setting, an incident beam angle and wavelength setting, a detector setting, a setting for the amount of reflected or transmitted light, or any other setting described herein, etc. The settings for the reflection and transmission modes may be empirically selected to maximize the sensitivity of inspection. Using the same recipe and the same tool to inspect the training and test reticle regions is preferred. Using different, but well-matched, tools for the training and test regions is possible.

The inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. A reticle image may be generated after all the positions of the reticle are scanned and converted into detected signals, or potions of a reticle image may be generated as each reticle portion is scanned with the final reticle image being complete after the entire reticle is scanned.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented.

The data for the detected signals for each set of one or more reticle portions or "patches" may be sent to parallel patch processors. For instance, the intensity values for a first patch may be sent to a first processor, and the intensity values for a second patch may be sent to a second processor. Alternatively, the data for a predefined number of patches may be sent to individual patch processors.

Figure 8:
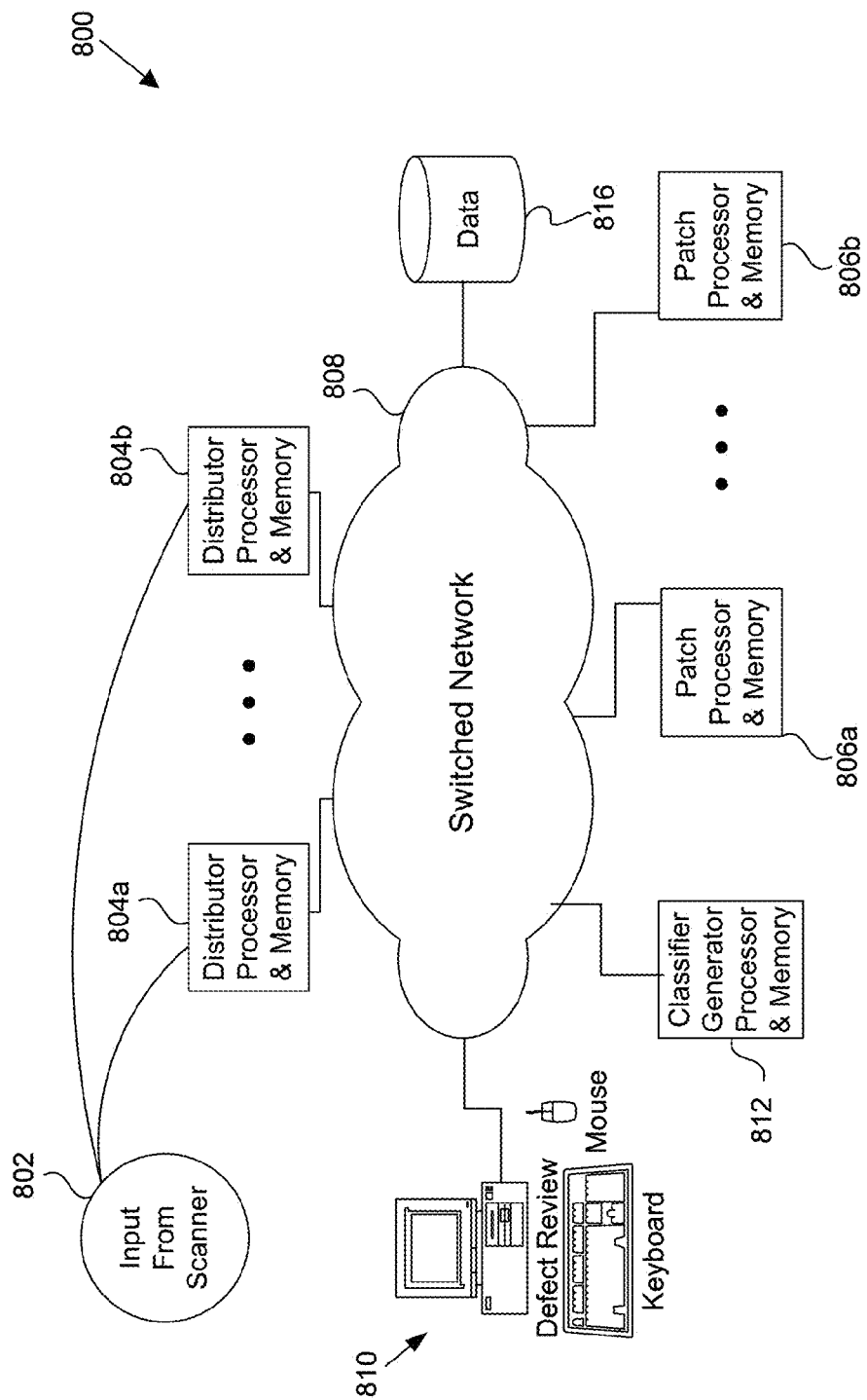
FIG. 8 is a diagrammatic representation of an example inspection system in which techniques of the present invention may be implemented

Techniques of the present invention may be implemented in any suitable combination of hardware and/or software. FIG. 8 is a diagrammatic representation of an example inspection system 800 in which techniques of the present invention may be implemented. The inspection system 800 may receive input 802 from an inspection tool or scanner (not shown). The inspection system may also include a data distribution system (e.g., 804a and 804b) for distributing the received input 802, an intensity signal (or patch) processing system (e.g., patch processors and memory 806a and 806b) for processing specific portions/patches of received input 802, a classifier generator system (e.g., Classifier Generator Processor and Memory 812) for generating a classifier, a network (e.g., switched network 808) for allowing communication between the inspection system components, an optional mass storage device 816, and one or more inspection control and/or review stations (e.g., 810) for reviewing the candidate defects. Each processor of the inspection system 800 typically may include one or more microprocessor integrated circuits and may also contain interface and/or memory integrated circuits and may additionally be coupled to one or more shared and/or global memory devices.

The scanner or data acquisition system (not shown) for generating input data 802 may take the form of any suitable instrument (e.g., as described further herein) for obtaining intensity signals or images of a reticle (or other specimen). For example, the scanner may construct an optical image or generate intensity values of a portion of the reticle based on a portion of detected light that is reflected, transmitted, or otherwise directed to one or more light sensors. The scanner may then output the intensity values or image may be output from the scanner.

Intensity or image data 802 can be received by data distribution system via network 808. The data distribution system may be associated with one or more memory devices, such as RAM buffers, for holding at least a portion of the received data 802. Preferably, the total memory is large enough to hold at least an entire swath of data. For example, one gigabyte of memory works well for a reticle swath of patches that is 1 million by 1000 pixels or points.

The data distribution system (e.g., 804a and 804b) may also control distribution of portions of the received input data 802 to the processors (e.g. 806a and 806b). For example, data distribution system may route data for a first patch to a first patch processor 806a, and may route data for a second patch to patch processor 806b. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well for intensity values or an image corresponding to a patch that is 512 by 1024 pixels. Alternatively, the patch processors may share memory.

Each set of input data 802 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 806*a*, and the second memory partition may hold and route second data to patch processor 806*b*.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

Figure 9A:
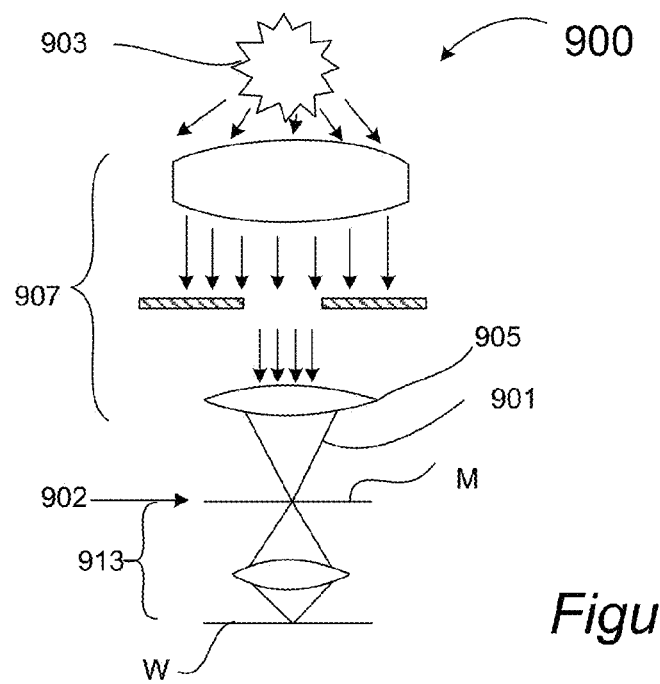
FIG. 9A is a simplified schematic representation of a lithographic system for transferring a mask pattern from a photomask onto a wafer in accordance with certain embodiments.

FIG. 9A is a simplified schematic representation of a typical lithographic system 900 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 903 directs a light beam through an illumination optics 907 (e.g., lens 905) onto a photomask M located in a mask plane 902. The illumination lens 905 has a numeric aperture 901 at that plane 902. The value of the numerical aperture 901 impacts which defects on the photomask are lithographic significant defects and which ones are not. A portion of the beam that passes through the photomask M forms a patterned optical signal that is directed through imaging optics 913 and onto a wafer W to initiate the pattern transfer.

Figure 9B:
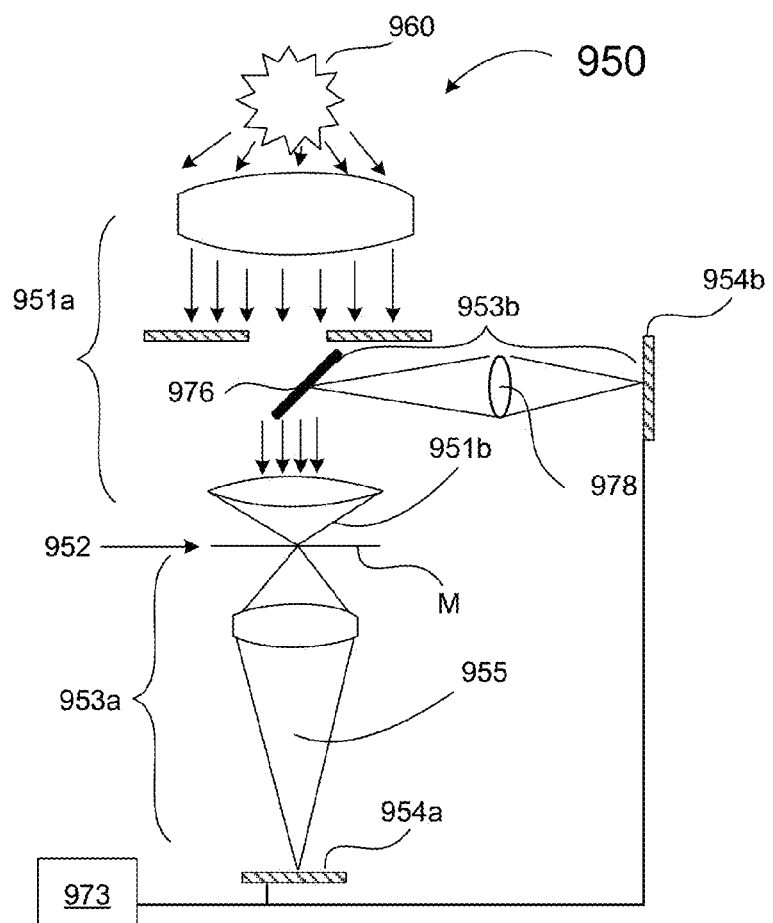
FIG. 9B provides a schematic representation of a photomask inspection apparatus in accordance with certain embodiments.

FIG. 9B provides a schematic representation of an example inspection system 950 that has illumination optics 951*a* includes an imaging lens with a relative large numerical aperture 951*b* at a reticle plane 952 in accordance with certain embodiments. The depicted inspection system 950 includes detection optics 953*a* and 953*b*, including microscopic magnification optics designed to provide, for example, 60-200× magnification or more for enhanced inspection. For example, the numerical aperture 951*b* at the reticle plane 952 of the inspection system may be considerable greater than the numerical aperture 901 at the reticle plane 902 of the lithography system 900, which would result in differences between test inspection images and actual printed images.

The inspection techniques described herein may be implemented on various specially configured inspection systems, such as the one schematically illustrated in FIG. 9B. The illustrated system 950 includes an illumination source 960 producing a light beam that is directed through illumination optics 951*a* onto a photomask M in the reticle plane 952. As explained above, the inspection system 950 may have a numerical aperture 951*b* at the reticle plane 952 that may be greater than a reticle plane numerical aperture (e.g., element 901 in FIG. 9A) of the corresponding lithography system. The photomask M to be inspected is placed on a mask stage at the reticle plane 952 and exposed to the source.

The transmitted image from the mask M is directed through a collection of optical elements 953*a*, which project the patterned image onto a sensor 954*a*. Optical elements (e.g., beam splitter 976 and detection lens 978) are arranged to direct and capture the reflected light onto sensor 954*b*. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 954*a* and/or 954*b*) can be processed by a computer system 973 or, more generally, by one or more signal processing devices, which may each include an analog-to-digital converter configured to convert analog signals from each sensor into digital signals for processing. The computer system 973 typically has one or more processors coupled to input/output ports, and one or more memories via appropriate buses or other communication mechanisms.

The computer system 973 may also include one or more input devices (e.g., a keyboard, mouse, joystick) for providing user input, such as changing focus and other inspection recipe parameters. The computer system 973 may also be connected to the stage for controlling, for example, a sample position (e.g., focusing and scanning) and connected to other inspection system components for controlling other inspection parameters and configurations of such inspection system components.

The computer system 973 may be configured (e.g., with programming instructions) to provide a user interface (e.g., a computer screen) for displaying resultant intensity values, images, and other inspection results. The computer system 973 may be configured to generate a 3D (or more) classifier or 3D (or more) test feature space, analyze intensity, phase, and/or other characteristics of reflected and/or transmitted sensed light beam. The computer system 973 may be configured (e.g., with programming instructions) to provide a user interface (e.g., on a computer screen) for displaying resultant intensity values, images, and other inspection characteristics. In certain embodiments, the computer system 973 is configured to carry out inspection techniques detailed above Because such information and program instructions may be implemented on a specially configured computer system, such a system includes program instructions/computer code for performing various operations described herein that can be stored on a non-transitory computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a specimen, the method comprising:
   using an inspection system at one or more operating modes, obtaining images of a plurality of training regions of a specimen, wherein the training regions are identified as defect-free;
   deriving three or more basis training images from the images of the training regions;
   forming a classifier by constructing a manifold approximating points in a feature space, the feature space having three or more dimensions corresponding to three or more basis images;
   using the inspection system at the one or more operating modes, obtaining images of a plurality of test regions of a specimen;
   deriving three or more basis test images from the test regions; and
   applying the classifier to the three or more basis test images to find defects in the test regions.

2. The method of claim 1, wherein forming the classifier includes:
   mapping the three or more basis training images to a plurality of voxels of the feature space; and
   assigning an observation indicator to each voxel so as to specify whether such voxel is defined as a non-defective voxel that is observed in the training set.

3. The method of claim 2, wherein forming the classifier further includes:
   healing a plurality of holes in the non-defective voxels by changing an indicator of each voxel of each hole from specifying such voxel is not observed in the training set to specifying that such voxel is a non-defective voxel.

4. The method of claim 3, wherein forming the classifier further includes performing a distance transformation to assign a distance value to each voxel based on such voxel's distance to a non-defective voxel.

5. The method of claim 4, wherein a defect is found when a particular voxel has a distance value that is above a predefined threshold.

6. The method of claim 1, further comprising:
   forming each of a plurality of classifiers based on a plurality of different sets of the three or more basis training images; and
   applying the plurality of classifiers to the three or more basis test images to find defects in the test regions.

7. The method of claim 1, further comprising forming a space-partitioning data structure from the classifier.

8. The method of claim 2, wherein forming the classifier comprises approximating a set of feature vectors that correspond to the non-defective voxels with a collection of subsets of affine-linear spaces.

9. The method of claim 1, wherein forming the classifier comprises:
   clustering a set of feature vectors that are based on the basis training images into a plurality of clusters;
   determining a cluster center of each cluster's feature vectors;
   for each cluster, determining a plurality of cluster vectors from each cluster center to the cluster's feature vectors; and
   for each cluster, determining an affine-linear space that includes the cluster's cluster center and that is spanned by a plurality of principal components of the cluster's cluster vectors,
   wherein applying the classifier to the three or more basis test images is based on a distance between each test vector of the three or more basis test images and a nearest affine-linear space.

10. The method of claim 1, wherein forming the classifier comprises:
    minimizing a norm of distances from a affine linear space to a plurality of feature vectors from the three or more basis training images;
    discarding a set of the feature vectors for which a distance is highest; and
    repeating the step for minimizing the norm of distance to refine a plurality of affine-linear spaces to better fit remaining ones of the feature vectors until the feature vectors are fitted to a final set of the affine-linear spaces within a predefined tolerance level.

11. The method of claim 1, wherein the classifier includes three or more dimensions of feature vectors that each has a transmitting image value, a reflecting image value, and a transformed image value based on transformation of a transmitting or reflecting image value.

12. The method of claim 11, wherein each transformed image value is determined by one of the following: $\|\nabla T\|$, $\|\nabla R\|, \nabla^2 T, \nabla^2 R$, wherein T is a transmitting image value and R is a reflecting image value.

13. The method of claim 1, wherein the one or more operating modes are selectable to differ in one or more of the following qualities or quantities: a reflecting mode, a transmitting mode, a brightfield mode, a darkfield mode, an illumination numerical aperture, an illumination pupil pattern, an illumination polarization, a collection numerical aperture, a collection pupil filter amplitude and phase, a collection analyzer, and a focus.

14. An inspection system for inspecting a specimen, the system comprising at least one memory and at least one processor that are configured to perform the following operations:
    at one or more operating modes of the inspection system, obtaining images of a plurality of training regions of a specimen, wherein the training regions are identified as defect-free;
    deriving three or more basis training images from the images of the training regions;
    forming a classifier by constructing a manifold approximating points in a feature space, the feature space having three or more dimensions corresponding to three or more basis images;
    at the one or more operating modes, obtaining images of a plurality of test regions of a specimen; and
    deriving three or more basis test images from the test regions; and
    applying the classifier to the three or more basis test images to find defects in the test regions.

15. The inspection system of claim 14, wherein forming the classifier includes:
    mapping the three or more basis training images to a plurality of voxels of the feature; and
    assigning an observation indicator to each voxel so as to specify whether such voxel is defined as a non-defective voxel that is observed in the training set.

16. The inspection system of claim 15, wherein forming the classifier further includes:
 healing a plurality of holes in the non-defective voxels by changing an indicator of each voxel of each hole from specifying such voxel is not observed in the training set to specifying that such voxel is a non-defective voxel.

17. The inspection system of claim 16, wherein forming the classifier further includes performing a distance transformation to assign a distance value to each voxel based on such voxel's distance to a non-defective voxel.

18. The inspection system of claim 17, wherein a defect is found when a particular voxel has a distance value that is above a predefined threshold.

19. The inspection system of claim 14, wherein the at least one memory and at least one processor are further configured for:
 forming each of a plurality of classifiers based on a plurality of different sets of the three or more basis training images; and
 applying the plurality of classifiers to the three or more basis test images to find defects in the test regions.

20. The inspection system of claim 14, wherein the at least one memory and at least one processor are further configured for forming a space-partitioning data structure from the classifier.

21. The inspection system of claim 15, wherein forming the classifier comprises approximating a set of feature vectors that correspond to the non-defective voxels with a collection of subsets of affine-linear spaces.

22. The inspection system of claim 14, wherein forming the classifier comprises:
 clustering a set of feature vectors that are based on the basis training images into a plurality of clusters;
 determining a cluster center of each cluster's feature vectors;
 for each cluster, determining a plurality of cluster vectors from each cluster center to the cluster's feature vectors; and
 for each cluster, determining an affine-linear space that includes the cluster's cluster center and that is spanned by a plurality of principal components of the cluster's cluster vectors,
 wherein applying the classifier to the three or more basis test images is based on a distance between each test vector of the three or more basis test images and a nearest affine-linear space.

23. The inspection system of claim 14, wherein forming the classifier comprises:
 minimizing a norm of distances from a affine linear space to a plurality of feature vectors from the three or more basis training images;
 discarding a set of the feature vectors for which a distance is highest; and
 repeating the step for minimizing the norm of distance to refine a plurality of affine-linear spaces to better fit remaining ones of the feature vectors until the feature vectors are fitted to a final set of the affine-linear spaces within a predefined tolerance level.

24. The inspection system of claim 14, wherein the classifier includes three or more dimensions of feature vectors that each has a transmitting image value, a reflecting image value, and a transformed image value based on transformation of a transmitting or reflecting image value.

25. The inspection system of claim 24, wherein each transformed image value is determined by one of the following: $\|\nabla T\|, \|\nabla R\|, \nabla^2 T, \nabla^2 R$, wherein T is a transmitting image value and R is a reflecting image value.

26. The inspection system of claim 14, wherein the one or more operating modes are selectable to differ in one or more of the following qualities or quantities: a reflecting mode, a transmitting mode, a brightfield mode, a darkfield mode, an illumination numerical aperture, an illumination pupil pattern, an illumination polarization, a collection numerical aperture, a collection pupil filter amplitude and phase, a collection analyzer, and a focus.

* * * * *